United States Patent [19]

Downs et al.

[11] Patent Number: 5,532,587

[45] Date of Patent: Jul. 2, 1996

[54] MAGNETIC FIELD ANALYSIS METHOD AND APPARATUS FOR DETERMINING STRESS CHARACTERISTICS IN A PIPELINE

[75] Inventors: Robert W. Downs, Houston; James C. Simek, Richmond, both of Tex.

[73] Assignee: Vetco Pipeline Services, Inc., Houston, Tex.

[21] Appl. No.: 808,425

[22] Filed: Dec. 16, 1991

[51] Int. Cl.$^6$ .......................... G01N 27/72; G01N 27/82; G01R 33/12

[52] U.S. Cl. .............................................. 324/220; 324/242

[58] Field of Search .................................. 324/209, 219, 324/220, 221, 238, 240, 242

[56] References Cited

U.S. PATENT DOCUMENTS

| | | | |
|---|---|---|---|
| 2,686,039 | 8/1954 | Bender | 324/209 |
| 2,698,920 | 1/1955 | Gieske | 324/221 |
| 3,015,063 | 12/1961 | Ownby . | |
| 3,202,914 | 8/1965 | Deem et al. . | |
| 3,243,697 | 3/1966 | Schmidt | 324/221 |
| 3,284,701 | 11/1966 | Kerbow . | |
| 3,484,682 | 12/1969 | Wood . | |
| 3,609,530 | 9/1971 | Johnson . | |
| 3,786,684 | 1/1974 | Wiers et al. . | |
| 3,899,734 | 8/1975 | Beaver et al. . | |
| 3,949,292 | 4/1976 | Beaver et al. . | |
| 3,967,194 | 6/1976 | Beaver et al. . | |
| 4,087,749 | 5/1978 | McCormack . | |
| 4,634,976 | 1/1987 | Tiitto et al. . | |
| 4,814,705 | 3/1989 | Saunderson . | |
| 4,964,059 | 10/1990 | Sugaya et al. . | |

FOREIGN PATENT DOCUMENTS

| | | |
|---|---|---|
| 934354 | 7/1982 | U.S.S.R. . |
| 2159954 | 12/1985 | United Kingdom . |

OTHER PUBLICATIONS

New Scandinavian Technology "The Electrical 'Fingerprint'"–a current Method, No. 1 Printed by Svenska Tryckcentralen AB, in Stockholm, Sweden in May 1992.

Langman, R., "The Effect of Stress on the Magnetization of Mild Steel at Moderate Field Strengths", IEEE Transactions on Magnetics, vol. Mag–21, No. 4, pp. 1314–1320 (Jul. 1985).

Atherton, D. L. et al., "Stress–Induced Magnetization Changes of Steel Pipes–Laboratory Tests, Part II", IEEE Transactions on Magnetics, vol. Mag–20, No. 6, pp. 2129–2136 (Nov. 1984).

Atherton, D. L. et al., Stress Induced Magnetization Changes of Steel Pipes–Laboratory Tests, IEEE Transactions on Magnetics, vol. Mag.–19, No. 4. pp. 1564–1568 (Jul. 1983).

Primary Examiner—W. Snow
Attorney, Agent, or Firm—Vaden, Eickenroht & Thompson

[57] ABSTRACT

The apparatus of the invention is a segmented pig body having an electrical instrumentation subassembly mounted thereto. The subassembly consists of a plurality sensors for electromagnetically coupling to the inner surface of the pipeline, each of which generates a signal that varies as the localized relative permeability of the pipeline metal; an odometer assembly for generating correlating data; and an instrument for recording the signal and data for later analysis. The method of the invention comprises passing the pig through the pipeline while it is electromagnetically coupled by the sensors to the inner surface of the pipeline. During the pass, signals varying with the localized magnetic permeability of the pipeline wall and correlative data are generated and recorded. After the pass, the correlative data is used to correlate the signals to wall locations to locate stress occurrences.

6 Claims, 3 Drawing Sheets

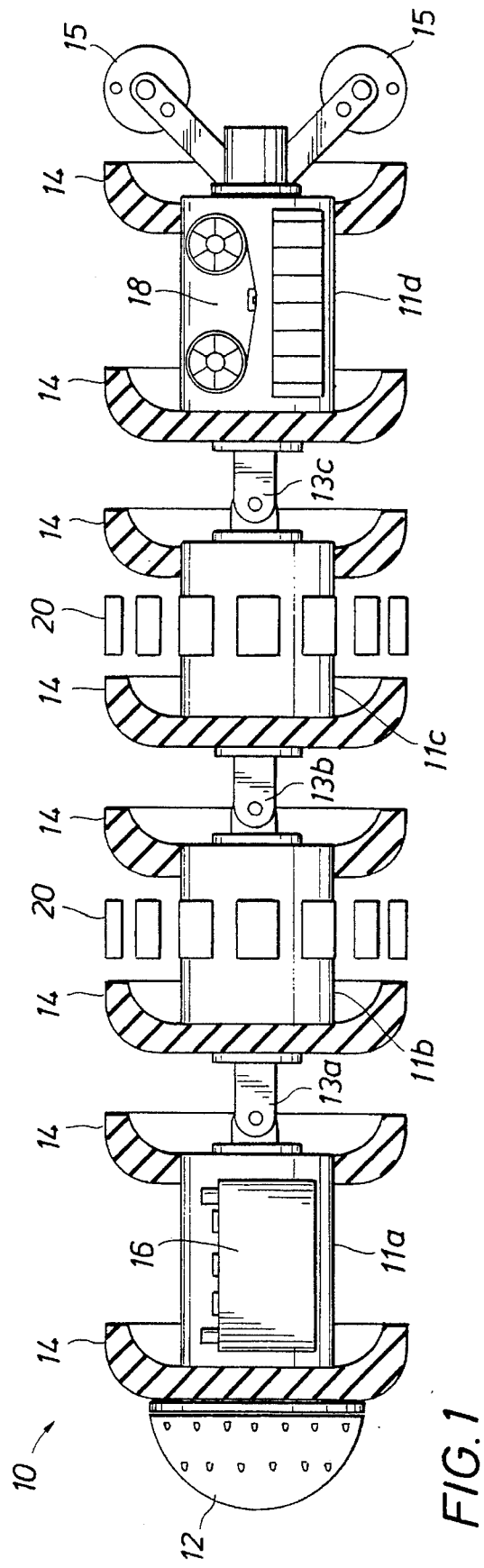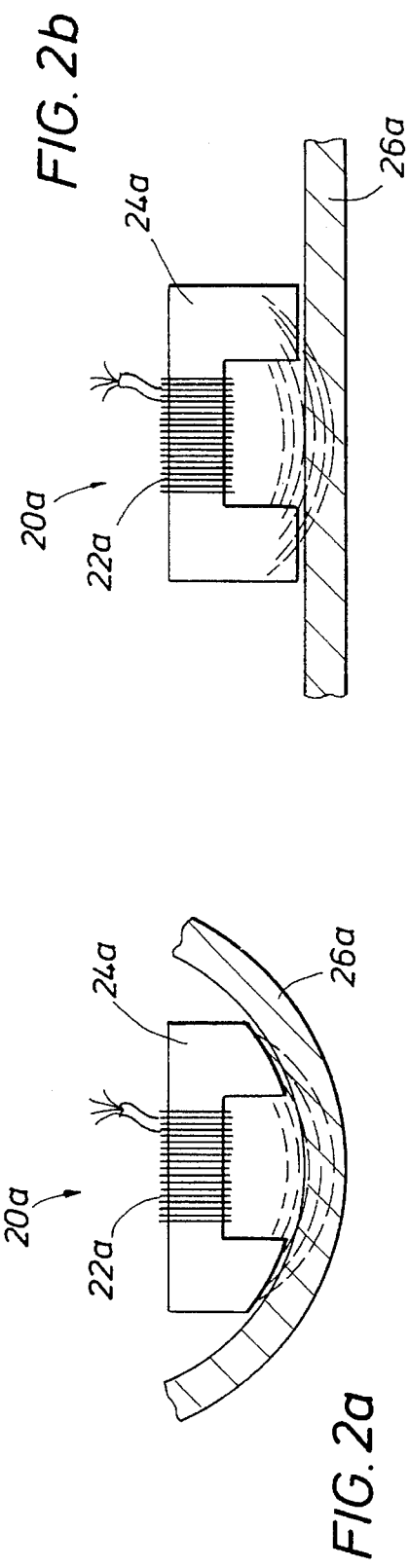
FIG. 1
FIG. 2a
FIG. 2b

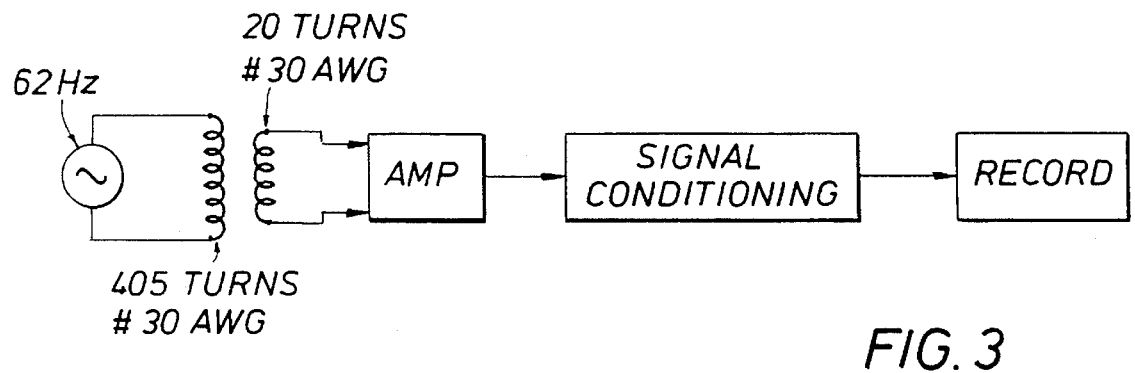
FIG. 3
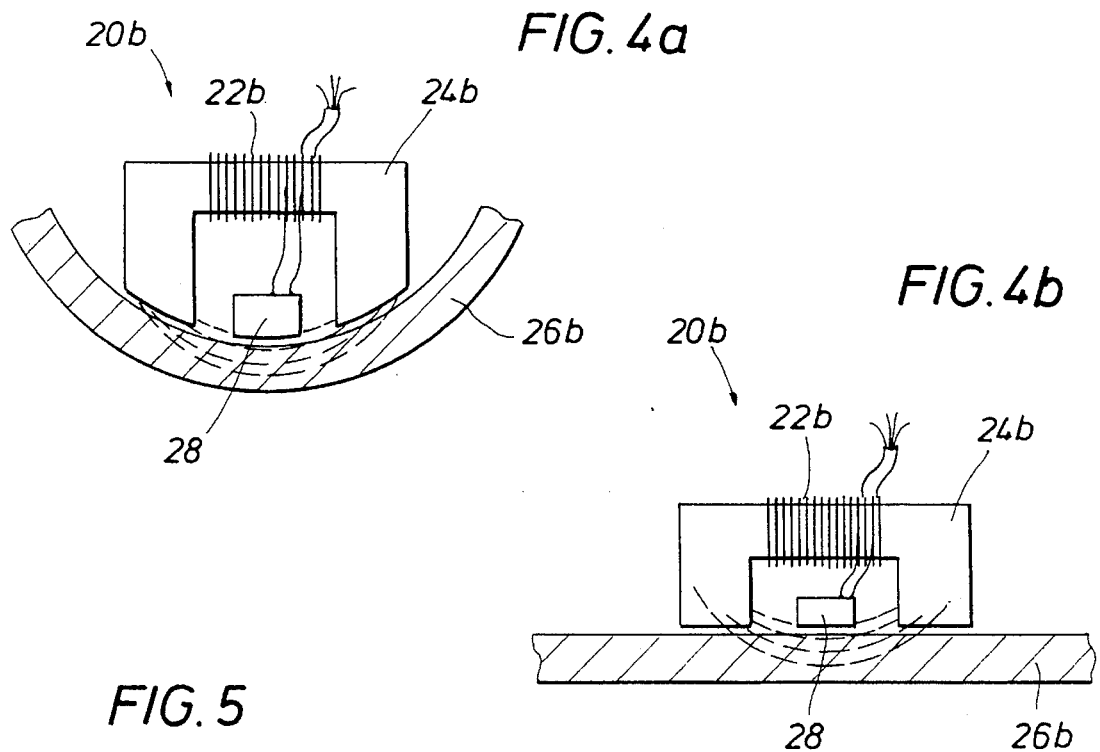
FIG. 4a
FIG. 4b
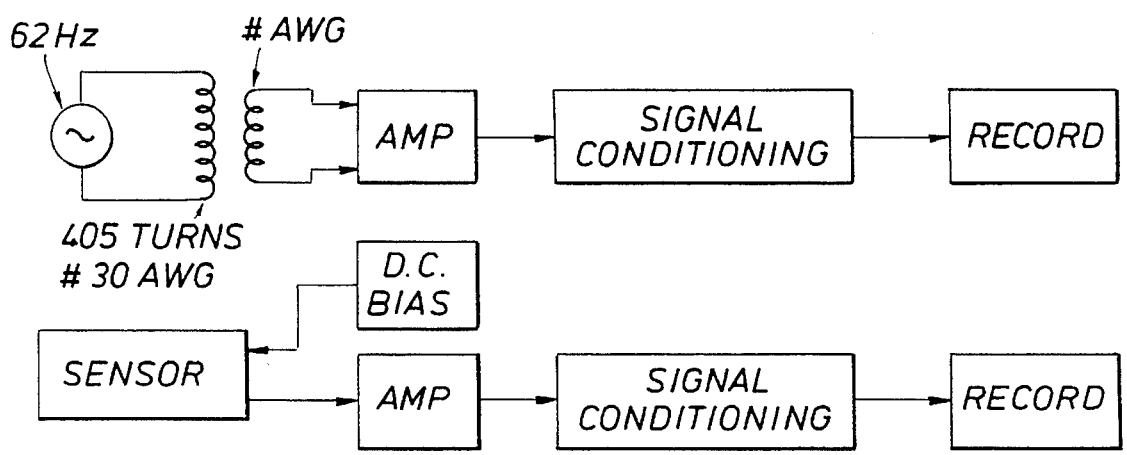
FIG. 5

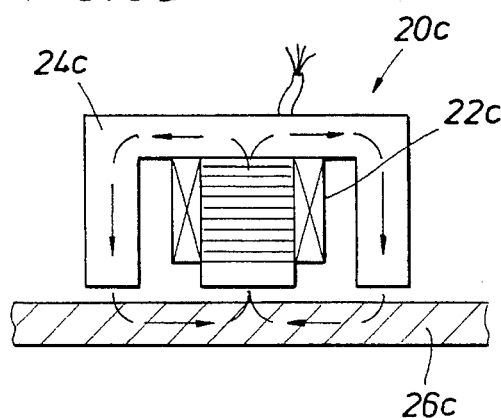
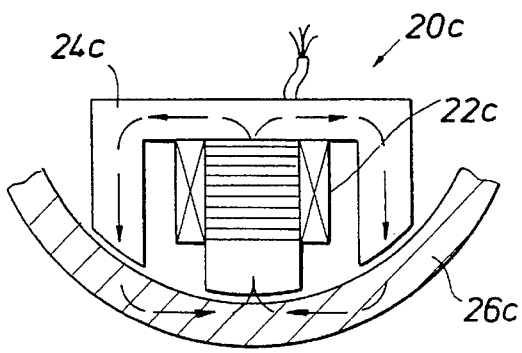
FIG. 6a    FIG. 6b
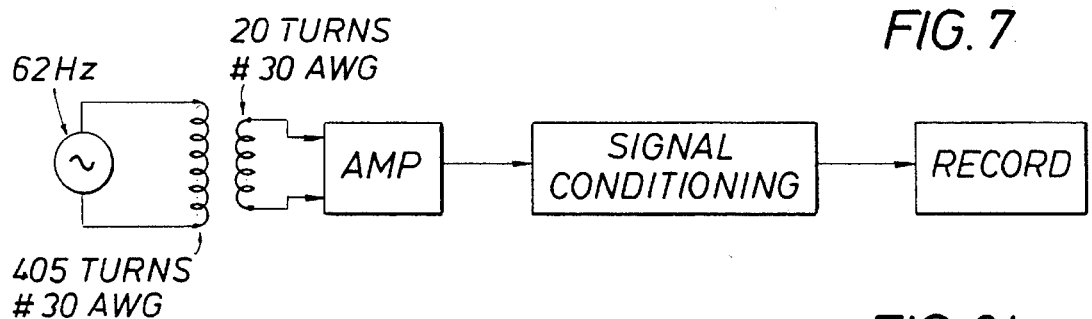
FIG. 7
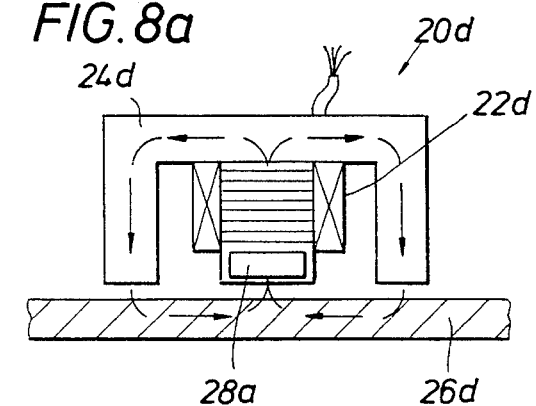
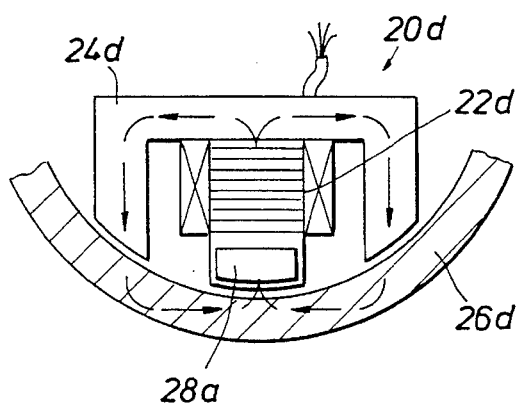
FIG. 8a    FIG. 8b
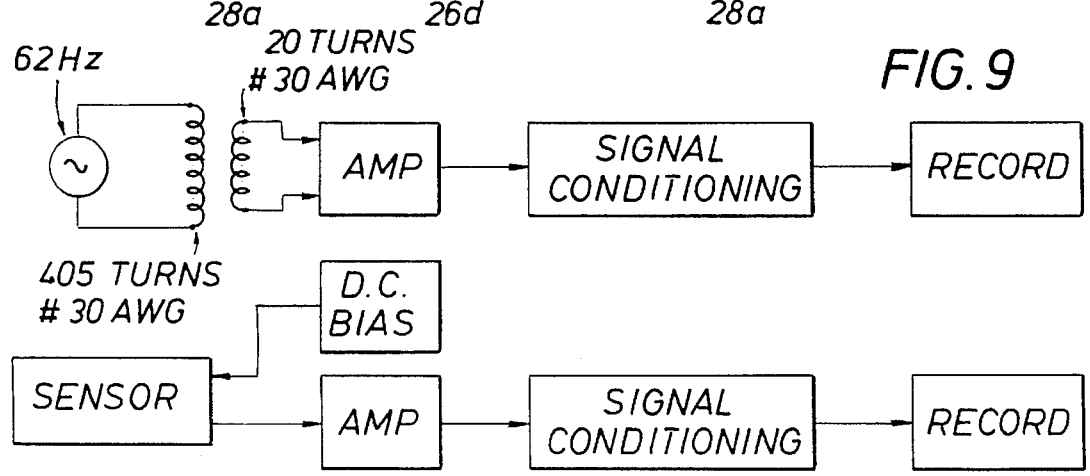
FIG. 9

MAGNETIC FIELD ANALYSIS METHOD AND APPARATUS FOR DETERMINING STRESS CHARACTERISTICS IN A PIPELINE

FIELD OF THE INVENTION

This invention pertains to inspection and location of stress occurrences in a pipeline wall. More specifically, this invention pertains to an apparatus and a method for using the apparatus to locate and map occurrences of stress in pipeline walls to facilitate maintenance and repair of pipelines.

DESCRIPTION OF THE PRIOR ART

The pipeline industry has always been strongly motivated to maintain the integrity of its pipelines systems and for years has induced manufacturers and service companies to develop better testing and inspection equipment. Previous efforts at non-destructive inspection have aimed at locating and evaluating specific anomalies that are injurious to pipelines. Specifically:

1.) pipeline wall corrosion which can continually reduce pipeline wall thickness resulting in increasing localized stress;
2.) gouging, also a stress concentrator-type defect, that leads to rapid failure in the presence of typical pipeline pressure cycling;
3.) physical deformations such as dents that lead to localized corrosion in the presence of stress concentration;
4.) hard spot formation which can lead to hydrogen stress cracking and eventual failure occurring over time due to typical pipeline pressure cycling;
5.) curvature or bending that leads to buckling and failure when the elastic limit of the pipeline metal is exceeded;
6.) stress corrosion cracking, resulting in failure when the cumulative critical crack length of individual crack is achieved.

All of the above phenomena can cause pipeline failure if they are not found and eliminated prior to the localized stress reaching critical limits. Manifestations of localized stress have a number of fundamentally different orientations including radial, circumferential, and longitudinal.

Thus, the single most significant parameter in the analysis of failure in ferromagnetic pipeline grade steels is stress. This stress is typically manifested in a reduction in cross-sectional area of the pipeline wall that tends to further concentrate and increase stress thereby accelerating failure. Early detection and elimination can therefore help prevent pipeline failure.

It is known that stress affects the relative magnetic permeability of the ferromagnetic material of the pipe. Academic studies have been conducted in an effort to determine how and to what extent magnetic permeability is affected, among them:

1.) Atherton, et. al., "Stress Induced Magnetization Changes of Steel Pipes—Laboratory Tests", *IEEE Transactions on Magnetics*; Vol. 19, No. 4, pp. 1564–1568 (July 1983);
2.) Atherton, et. al., "Stress Induced Magnetization Changes of Steel Pipes—Laboratory Tests", *IEEE Transactions on Magnetics*; Vol. 20, No. 6, pp. 2129–2136 (Nov. 1984); and
3.) Langman, "The Effect of Stress on the Magnetization of Mild Steel at Moderate Field Strengths", *IEEE Transactions on Magnetics*; Vol. 21, No. 4, pp. 1314–1320 (July 1985). Little progress has been made, however, in applying this knowledge for practical uses. As indicated by the first Atherton, et. al. article, stress induced change in relative permeability has not been widely investigated and field conditions hamper transfer of what knowledge there is to the real world.

One common instrument used in inspection and testing of pipelines is known as a "pig". A pig is essentially a cylindrical or spherical instrument that is run or "passed" through a preselected length of the pipeline. Some pigs are very primitive for simple tasks such as cleaning. Others are very sophisticated and carry electronic instrumentation for uses such as testing. The second Atherton, et. al., article suggested that a suitably instrumented pig might be used for inspecting pipelines for stress. Nobody, however, has ever achieved a viable design. Atherton, et. al., however, stated that "near-saturation" flux densities in the pipewall would be necessary.

Vetco Pipeline Services, Inc. has previously used the electromagnetic properties in pipeline inspection and testing. Some years ago, two pipe samples were provided to Vetco by a customer as test pieces to determine Vetco's capability to distinguish them based on pipe grade alone. All other parameters of the pipe were the same. The magnetic properties of the two samples were evaluated and the resultant B/H curves indicated reasonable probability that one could be distinguished from the other based on variances of magnetic permeability. A simple hand-held apparatus was first designed using ring core excitation with a Hall device sensor located in the gap to monitor the leakage flux. The device generated only very minor flux densities. A modified design extrapolated from the first was tested and found to be sensitive enough to fulfill the contract requirements. The device was then run through the pipeline and all of the unwanted grade pipe was identified and located for removal.

Additional evaluation of the data surprisingly showed that there were unexpected baseline offsets that could be correlated with known bends in the pipeline. It was shown that on the inside of the bends the shift was negative and on the outside it was positive. Vetco then concluded that these baseline shifts were the result of compressional and tensional stresses induced into the pipe due to the "free stress" bending of the pipe as it was lain to conform to the terrain.

Prompted by this revelation, Vetco investigated stored records for other occurrences of unexplained baseline shifting. The records were obtained previously during normal instrumented pigging (primarily for detection of three-dimensional body wall deterioration and deformation) but no occurrences were found using the conventional Vetcolog equipment. However, Vetco had previously designed and built a very special instrumented pig. One of the special considerations was that the pig had to be able to clearly ascertain wall thickness changes among the various joints of pipe along the pipeline from the data recorded. Vetco consequently added three channels of wall thickness information to the data presentation derived from three different sensors equally spaced around the circumference.

The sensors of the specially instrumented pig were magneto-diodes as are used for corrosion detection, but DC coupled to provide a baseline shift in the presence of higher or lower relative magnetic excitation as would be present as the wall thickness changed. Natural wall thickness changes theoretically occur for an entire joint. However, there were many instances of baseline shifting noted on the surveys that occurred in only a portion of a joint of pipe. Since there were always some type of physical anomaly such as a buckle or a bend that could be correlated to the locations of shifting and since Vetco was focusing on each joint in its entirety, the shifting was disregarded in the analysis for this job.

A comprehensive review of the survey data from the specially instrumented pig was made and correlated to a subsequent survey made on the same pipeline at a later date. Since the later survey also contained very accurate deformation data, the resulting conclusion was even more meaningful. It was now evident that the wall-thickness channels on the earlier survey were sensitive to changes in stress level in the pipeline induced by bending and other forms of deformation.

Although Atherton, et. al., and others in the art concluded that a practical application of the magnetic principles to detection and location of stress would require flux densities of "near-saturation", it now appeared that much lower levels could be used. It was furthermore evident that occurrences of stress could be located in many manifestations and orientations. Finally, it was apparent that a practical application could be developed from existing technology.

It is therefore a feature of this invention that it provides an improved procedure that utilizes changes in magnetic permeability in pipeline materials to detect and locate occurrences of stress.

It is a further feature of this invention that it provides an improved procedure that detects and locates occurrences of stress by employing low-level flux densities.

It is still a further feature of this invention that it provides an improved procedure that can be deployed in conventional fashion and constructed using existing technology adapted to this special purpose.

SUMMARY OF THE INVENTION

The apparatus of the invention is an instrumented means comprised of a segmented pig body having an electrical instrumentation subassembly mounted thereto. The subassembly consists of a plurality of means for electromagnetically coupling to the inner surface of the pipeline, each of which generates a signal that varies as the localized relative permeability of the pipeline metal; a means for generating data for correlating the signal to pipeline wall locations; and a means for recording the signal and data for later analysis. The method of the invention comprises passing the instrumented means through the pipeline while the instrumented means is electromagnetically coupled to the inner surface of the pipeline. During the pass, signals varying with the localized magnetic permeability of the pipeline wall and correlative data are generated and recorded. After the pass, the correlative data is used to correlate the signals to wall locations to locate stress occurrences.

BRIEF DESCRIPTION OF THE DRAWINGS

A more particular description of the invention briefly summarized above may be had by reference to the exemplary preferred embodiments illustrated in the drawings nevertheless illustrate only typical, preferred embodiments of the invention and are not to be considered limiting of its scope as the invention may admit to other equally effective embodiments.

In the Drawings;

FIG. 1 illustrates the apparatus of the invention in its preferred embodiment;

FIGS. 2a and 2b show the magnetic coupling, or sensing, means of the apparatus in FIG. 1 in its first preferred embodiment in a transverse and a longitudinal orientation, respectively, relative to the pipeline;

FIG. 3 is a schematic of the magnetic coupling means of FIGS. 2a and 2b in the electrical instrumentation subassembly of the apparatus of FIG. 1;

FIGS. 4a and 4b show the magnetic coupling, or sensing, means of the apparatus in FIG. 1 in its second preferred embodiment in a transverse and a longitudinal orientation, respectively, relative to the pipeline;

FIG. 5 is a schematic of the magnetic coupling means of FIGS. 4a and 4b in the electrical instrumentation subassembly of the apparatus in FIG. 1;

FIGS. 6a and 6b show the magnetic coupling, or sensing, means of the apparatus in FIG. 1 in its third preferred embodiment in a transverse and a longitudinal orientation, respectively, relative to the pipeline;

FIG. 7 is a schematic of the magnetic coupling means of FIGS. 6a and 6b in the electrical instrumentation subassembly of FIG. 1;

FIGS. 8a and 8b show the magnetic coupling, or sensing, means of the apparatus in FIG. 1 in its fourth preferred embodiment in a transverse and a longitudinal orientation, respectively, relative to the pipeline; and FIG. 9 is a schematic of the magnetic coupling means of FIGS. 8a and 8b in the electrical instrumentation subassembly of FIG. 1.

DESCRIPTION OF THE PREFERRED EMBODIMENTS

An instrumented means, generally denoted by the number 10, for use in inspecting pipelines for stress occurrences is illustrated in FIG. 1. Instrumented means 10 in the preferred embodiment is a Vetcolog pig manufactured by Vetco Pipeline Services, Inc. modified by a plurality of sensors 20. Instrumented means 10 includes means for generating correlating data 15, means for recording data 18, and means for providing power 16.

The typical pig body in the preferred embodiment of instrumented means 10 comprises bumper assembly 12 mounted to lead body segment 11a and having centralizing cups 14 mounted to body segments 11a–d. Bumper assembly 12 absorbs shock arising from contact with obstructions. Centralizing cups 14 are constructed of polyurethane to resist wear and ensure that instrumented means 10 remains relatively centered in the pipeline. Body segments 11a–d are joined by high efficiency universal joints 13a–c that allow instrumented means 10 to traverse bends and other physical obstacles encountered in pipelines.

The pig body is also equipped with an electrical instrumentation subassembly according to its use. The subassembly for purposes of the invention includes a sensor mounting assembly (not shown) as is known to the art, power means 16, data acquisition system 18, and odometer assembly 15 as well as all necessary interconnect wiring and harnessing (also not shown) for transmission of data and power. Transmission of data and power may be either from the surface to the pig body or among components of the electrical instrumentation subassembly.

Power means 16 is a battery pressure sealed within body segment 11a to environmentally isolate the battery from the fluids in the pipeline. The battery must have sufficient capacity to operate the entire electrical instrument subsystem for the duration of the pass through the pipeline, if necessary. The selection of power means from the operating parameters in the present invention is the same as is practiced and well known in the art for instrumented pigs generally.

Data acquisition system 18 is powered by power means 16 and receives data from each of the plurality of magnetic coupling means 20 and odometer assembly 15. Data acquisition system 18 is also pressure sealed so that it is environmentally isolated from the fluids in the pipeline. Data acquisition system must be capable of accurately processing and permanently archiving all of the data generated by the plurality of sensors 20 and odometer assembly 15. The selection of data acquisition system 18 for any particular embodiment of the invention is also as is known and practiced in the art.

Odometer assembly 15 is powered by power means 16 and, like power means 16 and data acquisition system 18, is of a type well known in the art. Odometer assembly 15 consists of at least one wheel of a precisely known circumference rolling on the internal surface of the pipe without slippage and generating an output signal which, when processed, will provide accurate information as to the distance traveled as well as velocity of instrumented means 10 as it passes through the pipeline. The signal output by odometer assembly 18 is received and archived by data acquisition system 18.

A plurality of magnetic coupling means 20 powered by power means 16 are mounted to the sensor mounting assembly (not shown) of the pig body in a manner well known to the art. Each one of the plurality must be mounted and maintained in a precise circumferential position such that it is held snugly against the internal surface of the pipeline but not so tightly as to be unable to flex as necessary to pass over and through obstructions. Typical obstructions include bends, valves and dents.

As is illustrated in FIG. 1, the plurality of magnetic coupling means 20 is mounted to the pig body of instrumented means 10 so as to cover substantially all of the internal circumference of the pipeline. The preferred embodiment accomplishes this by mounting a first subset of the plurality to body segment 11b and a second subset to body segment 11c. The individual magnetic coupling means of the second subset being mounted to operate in the coverage gaps of the first subset with some overlap. Each one of the plurality of magnetic coupling means 20 generates and transmits a signal that is received and archived by data acquisition system 18.

The individual electromagnetic coupling means of the plurality 20 may be any one of four alternative embodiments 20a–d shown in FIGS. 2a–b, 4a–b, 6a–b, and 8a–b. FIGS. 2a–b, 4a–b, 6a–b, and 8a–b also illustrate that the embodiments can be oriented either transversely or longitudinally with respect to the direction of flow in the pipeline. The four alternative embodiments operate on much the same scientific principles and their operation in the electrical instrumentation subsystem is shown in FIGS. 3, 5, and 7, respectively.

The first alternative embodiment, generally denoted 20a, is shown in FIG. 2a in a transverse orientation and in FIG. 2b in a longitudinal orientation. The embodiment 20a comprises core 24a and winding 22a. Core 24a is constructed of a ferromagnetic material and is shaped to conform to the surface of pipe surface 26a. Winding 22a consists of a primary coil of approximately 405 turns of #30 AWG wire and a secondary coil of approximately 20 turns of #30 AWG wire.

The primary coil is pulsed at a rate of approximately 62 Hz to couple core 24a with pipe surface 26a and induce a magnetic flux in core 24a. As shown in FIG. 3, the output signal of the secondary coil is amplified, conditioned, and archived by recording means 18, all as are well known in the art. The archived signal then varies as the localized magnetic permeability varies in the pipeline.

The second alternative embodiment, generally denoted 20b, is shown in FIG. 4a in a transverse orientation and in FIG. 4b in a longitudinal orientation. Core 24b and winding 22b are substantially the same as core 24a and winding 22a but are operated in conjunction with flux density sensor 28. Flux density sensor 28 in the preferred embodiment is a magnetodiode but other types of flux density sensors may be equally satisfactory.

Core 24a and winding 22b are operated as described above for their counterparts in the first alternative embodiment. Flux density sensor 28 is DC biased by the presence of flux leakage near internal surface 26b of the pipeline and provides additional data that is sometimes valuable where the internal surface 26b is very rough or where the pipeline wall is very thin. The schematic of this embodiment is shown in FIG. 5 herein it is shown that sensor 28 generates an output signal that is also archived after being conditioned.

The third alternative embodiment, generally denoted as 20c, is shown in FIG. 6a in a transverse orientation and in FIG. 6b in a longitudinal orientation. The third embodiment comprises cup core 24c constructed of ferromagnetic material and formed to inner surface 26c of the pipeline. Winding 22c on cup core 24c consists of an approximately 405 turn primary coil and an approximate 20 turn secondary coil, both of #30 AWG wire. The schematic is shown in FIG. 7, which shows that the output of the secondary coil of winding 22c is amplified, conditioned, and archived.

A fourth embodiment, generally denoted as 20d, of the magnetic coupling, or sensing, means of the apparatus of FIG. 1 is illustrated in a transverse and longitudinal orientation, respectively, to the pipe. Cup core 24d is constructed of ferromagnetic material and conforms to inner surface 26d of the pipeline. Winding 22 consists of an approximately 405 turn primary coil and an approximate 20 turn secondary coil, both of #30 AWG wire. This embodiment differs from that of 6a and 6b by the addition of flux density sensor 28a, which operates as does flux density sensor 28 in FIGS. 4a and 4b. FIG. 9 is the schematic diagram of the electrical subassembly of the apparatus in FIG. 1 employing the preferred embodiment of FIGS. 8a and 8b.

In the method of the invention, instrumented means 10 is inserted and passed through a preselected length of pipeline in a manner consistent with pipeline pigs commonly known to those in the art. Once activated, instrumented means 10 is electromagnetically coupled to the inner surface of the pipeline by each of the plurality of electromagnetic coupling means 20 for the duration of the pass. The electrical instrument subassembly is deactivated when instrumented means 10 has completed the pass.

Once the pass is completed and instrumented means 10 removed from the pipeline, the data archived by recording means 18 is retrieved and analyzed. Techniques of correlating data generated by the plurality of coupling means 20 to the physical locations on the pipeline, using data generated by odometer assembly 15 and plurality of coupling means 20, are well known in the art and can therefore be easily extrapolated by one of ordinarily skill in the art.

The invention is not to be limited to the embodiments disclosed herein. For instance, although the preferred embodiment uses the odometer assembly to implement data generated by correlating data generating means 15, there are several other equally acceptable methods of correlating data generated by instrumented pigs. Since the welds between pipe joints create baseline shifts and appear at regular intervals, these baseline shifts can be used for correlation purposes. Likewise, powerful magnetic markers can be placed above ground over the pipeline to create known, characteristic baseline shifts. These and other such modifications as will be seen by others having the benefits of the teachings herein are considered to be within the scope and spirit of the invention claimed below.

What is claimed is:

1. An apparatus for use in detecting and locating occurrences of stress in the wall of a pipeline constructed of ferromagnetic metal, comprising:

means forming a pig body to be passed through the pipeline;

a plurality of means for magnetically coupling to the wall and for generating an electrical signal proportional to the density of the magnetic flux induced in each of the coupling means by the coupling, each of the coupling means being affixed to the body means;

means for generating correlating data;

means for recording the electric signal generated by each magnetic coupling means and for recording the correlating data generated by the data generating means; and means for powering each magnetic coupling means, the data generating means, and the recording means.

2. The apparatus of claim 1, wherein the plurality of magnetic coupling means are configured to magnetically couple with substantially all of the wall.

3. The apparatus of claim 1 or claim 2, wherein the correlating data is to be used to correlate magnetic flux density to the relative magnetic permeability of specific wall locations to determine the extent and orientation of stress occurrences.

4. The apparatus of claim 2 or claim 3, wherein at least one magnetic coupling means is at least one of a ferromagnetic core wound with a current bearing conductor, a ferromagnetic core wound with a current bearing conductor in combination with a flux density sensor, a cup core wound with a current bearing conductor, a permanent magnet core mounted with a current bearing conductor, and a permanent magnet core wound with a current bearing conductor coupled with a flux density sensor.

5. An apparatus for use in detecting and locating occurrences of stress in the wall of a pipeline constructed of ferromagnetic metal, comprising:

means forming a pig body to be passed through the pipeline;

a plurality of means for magnetically coupling to the wall and for generating an electrical signal proportional to the density of the magnetic flux induced in each of the coupling means by the coupling, the plurality of coupling means being configured to magnetically couple with substantially all of the wall and each one of the plurality of coupling means being affixed to the body means;

means for generating correlating data;

means for recording the electric signal generated by each magnetic coupling means and for recording the correlating data generated by the data generating means; and means for powering each magnetic coupling means, the data generating means, and the recording means.

6. An apparatus for use in detecting and locating occurrences of stress in the wall of a pipeline constructed of ferromagnetic metal, comprising:

means forming a pig body to be passed through the pipeline;

a plurality of means for magnetically coupling to the wall and for generating an electrical signal proportional to the density of the magnetic flux induced in each of the coupling means by the coupling, each of the coupling means being affixed to the body means;

means for generating correlating data, the correlating data to be used to correlate magnetic flux density to the relative magnetic permeability of specific wall locations to determine the extent and orientation of stress occurrences;

means for recording the electric signal generated by each magnetic coupling means and for recording the correlating data generated by the delta generating means; and means for powering each magnetic coupling means, the data generating means, and the recording means.

\* \* \* \* \*